US009205345B2

(12) United States Patent
Dobry et al.

(10) Patent No.: US 9,205,345 B2
(45) Date of Patent: *Dec. 8, 2015

(54) SPRAY-DRYING APPARATUS AND METHODS OF USING THE SAME

(71) Applicant: Bend Research, Inc., Bend, OR (US)

(72) Inventors: Daniel E. Dobry, Bend, OR (US); James M. Mullin, Bend, OR (US); Douglas L. Millard, Bend, OR (US)

(73) Assignee: Bend Research, Inc., Bend, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/617,776

(22) Filed: Feb. 9, 2015

(65) Prior Publication Data

US 2015/0157954 A1 Jun. 11, 2015

Related U.S. Application Data

(63) Continuation of application No. 13/820,483, filed as application No. PCT/US2011/050222 on Sep. 1, 2011.

(60) Provisional application No. 61/380,103, filed on Sep. 3, 2010.

(51) Int. Cl.
*B01D 1/20* (2006.01)
*B01J 2/04* (2006.01)
*A61K 9/16* (2006.01)
*A61K 31/137* (2006.01)
(Continued)

(52) U.S. Cl.
CPC ... *B01D 1/20* (2013.01); *A61K 9/16* (2013.01); *A61K 9/1682* (2013.01); *A61K 31/137* (2013.01); *A61K 38/22* (2013.01); *A61K 38/28* (2013.01); *B01D 1/18* (2013.01); *B01J 2/04* (2013.01)

(58) Field of Classification Search
None
See application file for complete search history.

(56) References Cited

U.S. PATENT DOCUMENTS 2,460,546 A  2/1949  Stephanoff
2,937,091 A  5/1960  Rosenberg
(Continued)

FOREIGN PATENT DOCUMENTS

DE  3229843  3/1983
EP  0113967  7/1984
(Continued)

OTHER PUBLICATIONS

Snyder. "Streamlining Spray Drying Process Design for Pulmonary Dry Powder Product Development: Application of Computational Fluid Dynamics to Aid System Scale-Up," *Respiratory Drug Delivery* vol. 1, pp. 207-216 (2008).
(Continued)

*Primary Examiner* — Mary F Theisen
(74) *Attorney, Agent, or Firm* — Klarquist Sparkman, LLP

(57) ABSTRACT

A spray-drying apparatus includes a drying chamber that has a first end, a second end, and at least one side wall extending between the first and second ends to define an interior of the drying chamber having a center axis. A nozzle can be positioned at the first end of the drying chamber and be configured to atomize liquid and spray the atomized liquid into the interior of the drying chamber at a maximum spray pattern angle relative to the center axis. A ratio of the length between the first end and second end to a maximum width between opposing internal surfaces of the interior of the drying chamber can be at least 5 to 1.

20 Claims, 8 Drawing Sheets

(51) Int. Cl.
  *A61K 38/22* (2006.01)
  *A61K 38/28* (2006.01)
  *B01D 1/18* (2006.01)

(56) References Cited

U.S. PATENT DOCUMENTS

| | | | |
|---|---|---|---|
| 3,557,864 A | 1/1971 | Berg |
| 3,621,902 A | 11/1971 | Okada et al. |
| 3,673,106 A | 6/1972 | Jonas et al. |
| 3,922,189 A | 11/1975 | Penders |
| 4,019,958 A | 4/1977 | Hell et al. |
| 4,089,120 A | 5/1978 | Kozischek |
| 4,201,756 A | 5/1980 | Saeman et al. |
| 4,209,912 A | 7/1980 | Barker |
| 4,380,491 A | 4/1983 | Joy et al. |
| 5,013,557 A | 5/1991 | Tai |
| 5,039,532 A | 8/1991 | Jost et al. |
| 5,135,611 A | 8/1992 | Cameron |
| 6,165,506 A | 12/2000 | Jain et al. |
| RE37,053 E | 2/2001 | Hanes et al. |
| 6,303,148 B1 | 10/2001 | Hennink et al. |
| 6,395,302 B1 | 5/2002 | Hennink et al. |
| 6,406,735 B2 | 6/2002 | Stein et al. |
| 6,497,903 B1 | 12/2002 | Hennink et al. |
| 6,589,557 B2 | 7/2003 | Straub et al. |
| 6,589,562 B1 | 7/2003 | Shefer et al. |
| 6,610,317 B2 | 8/2003 | Straub et al. |
| 6,740,310 B2 | 5/2004 | Edwards et al. |
| 6,740,631 B2 | 5/2004 | Shefer et al. |
| 6,800,297 B2 | 10/2004 | Altreuter et al. |
| 6,835,389 B1 | 12/2004 | Dohi et al. |
| 6,932,983 B1 | 8/2005 | Straub et al. |
| 6,942,868 B2 | 9/2005 | Edwards et al. |
| 6,977,087 B2 | 12/2005 | Edwards et al. |
| 6,998,393 B2 | 2/2006 | Jin et al. |
| 7,018,657 B2 | 3/2006 | Dickinson et al. |
| 7,060,296 B2 | 6/2006 | Hennink et al. |
| 7,078,057 B2 | 7/2006 | Kerkhof |
| 7,300,919 B2 | 11/2007 | Patton |
| 7,323,441 B2 | 1/2008 | Morazzoni et al. |
| 7,378,110 B2 | 5/2008 | Truong Le et al. |
| 7,404,828 B1 | 7/2008 | Nicola |
| 7,521,069 B2 | 4/2009 | Patton et al. |
| 7,780,988 B2 | 8/2010 | Beyerinck et al. |
| 7,928,089 B2 | 4/2011 | Morton et al. |
| 8,343,550 B2 | 1/2013 | Beyerinck et al. |
| 8,402,672 B2 | 3/2013 | Nielson |
| 2002/0146509 A1 | 10/2002 | Kodokian et al. |
| 2003/0104076 A1 | 6/2003 | Berkulin et al. |
| 2003/0124193 A1 | 7/2003 | Snyder et al. |
| 2003/0166509 A1 | 9/2003 | Edwards et al. |
| 2003/0185893 A1 | 10/2003 | Beyerinck et al. |
| 2003/0207776 A1 | 11/2003 | Shefer et al. |
| 2003/0215515 A1 | 11/2003 | Truong-Le et al. |
| 2004/0006276 A1 | 1/2004 | Demos et al. |
| 2004/0037905 A1 | 2/2004 | Bringe |
| 2004/0062778 A1 | 4/2004 | Shefer et al. |
| 2004/0076670 A1 | 4/2004 | Klinksiek et al. |
| 2004/0091535 A1 | 5/2004 | Vachon et al. |
| 2004/0092470 A1 | 5/2004 | Leonard et al. |
| 2004/0109894 A1 | 6/2004 | Shefer et al. |
| 2004/0145069 A1 | 7/2004 | Low |
| 2004/0176391 A1 | 9/2004 | Weers et al. |
| 2004/0184995 A1 | 9/2004 | Katsuma et al. |
| 2004/0191186 A1 | 9/2004 | Edwards et al. |
| 2004/0224019 A1 | 11/2004 | Shefer et al. |
| 2004/0234597 A1 | 11/2004 | Shefer et al. |
| 2005/0019270 A1 | 1/2005 | Finlay et al. |
| 2005/0031692 A1 | 2/2005 | Beyerinck et al. |
| 2005/0037996 A1 | 2/2005 | Beck et al. |
| 2005/0058710 A1 | 3/2005 | Straub et al. |
| 2005/0065047 A1 | 3/2005 | Shefer et al. |
| 2005/0112235 A1 | 5/2005 | Shefer et al. |
| 2005/0118208 A1 | 6/2005 | Bewert et al. |
| 2005/0158249 A1 | 7/2005 | Edwards et al. |
| 2005/0191246 A1 | 9/2005 | Bechtold-Peters et al. |
| 2006/0039987 A1 | 2/2006 | Batycky et al. |
| 2006/0068019 A1 | 3/2006 | Dalziel et al. |
| 2006/0093557 A1 | 5/2006 | Dickinson et al. |
| 2006/0121121 A1 | 6/2006 | Jin et al. |
| 2006/0127480 A1 | 6/2006 | Tobyn et al. |
| 2006/0141029 A1 | 6/2006 | Heller et al. |
| 2006/0141047 A1 | 6/2006 | Heller et al. |
| 2006/0142185 A1 | 6/2006 | Morazzoni et al. |
| 2006/0153912 A1 | 7/2006 | Habich et al. |
| 2006/0159625 A1 | 7/2006 | Tarara et al. |
| 2006/0165785 A1 | 7/2006 | Noga et al. |
| 2006/0210640 A1 | 9/2006 | Kerkhof |
| 2006/0257491 A1 | 11/2006 | Morton et al. |
| 2006/0263454 A1 | 11/2006 | Sugiyama et al. |
| 2006/0280691 A1 | 12/2006 | Wang et al. |
| 2006/0292081 A1 | 12/2006 | Morton et al. |
| 2007/0020197 A1 | 1/2007 | Galli et al. |
| 2007/0031490 A1 | 2/2007 | Loebenberg et al. |
| 2007/0042021 A1 | 2/2007 | Schiffrin et al. |
| 2007/0043030 A1 | 2/2007 | Morton et al. |
| 2007/0045100 A1 | 3/2007 | Wright |
| 2007/0134341 A1 | 6/2007 | Kipp et al. |
| 2007/0148236 A1 | 6/2007 | Babcock et al. |
| 2007/0166386 A1 | 7/2007 | Chinea et al. |
| 2007/0189979 A1 | 8/2007 | Zeng et al. |
| 2008/0057003 A1 | 3/2008 | Bechtold-Peters et al. |
| 2008/0124349 A1 | 5/2008 | Engstad et al. |
| 2008/0131514 A1 | 6/2008 | Truong-Le et al. |
| 2008/0181962 A1 | 7/2008 | Brzeczko et al. |
| 2008/0207476 A1 | 8/2008 | Artiga Gonzalez et al. |
| 2008/0229609 A1 | 9/2008 | Bronshtein |
| 2008/0248117 A1 | 10/2008 | Kolter et al. |
| 2008/0292707 A1 | 11/2008 | Babcock et al. |
| 2009/0011031 A1 | 1/2009 | Staniforth et al. |
| 2009/0038612 A1 | 2/2009 | Nilsson et al. |
| 2009/0269411 A1 | 10/2009 | Bellinghausen et al. |
| 2009/0270308 A1 | 10/2009 | Libin et al. |
| 2009/0285905 A1 | 11/2009 | Gordon et al. |
| 2012/0015924 A1 | 1/2012 | Friesen et al. |
| 2013/0193598 A1 | 8/2013 | Friesen et al. |

FOREIGN PATENT DOCUMENTS

| | | |
|---|---|---|
| EP | 0380219 | 8/1990 |
| EP | 0405598 | 1/1991 |
| EP | 0421581 | 4/1991 |
| EP | 0421582 | 4/1991 |
| EP | 0807431 | 11/1997 |
| EP | 1239844 | 9/2002 |
| EP | 1506996 | 2/2005 |
| EP | 1552815 | 7/2005 |
| EP | 1552817 | 7/2005 |
| EP | 1741424 | 1/2007 |
| EP | 1844758 | 10/2007 |
| GB | 918168 | 2/1963 |
| GB | 1305598 | 2/1973 |
| GB | 2132495 | 7/1984 |
| WO | WO97/44013 | 11/1997 |
| WO | WO98/31346 | 7/1998 |
| WO | WO00/13672 | 3/2000 |
| WO | WO00/72827 | 12/2000 |
| WO | WO01/45674 | 6/2001 |
| WO | WO01/45677 | 6/2001 |
| WO | WO01/78689 | 10/2001 |
| WO | WO01/95877 | 12/2001 |
| WO | WO02/24169 | 3/2002 |
| WO | WO02/45575 | 6/2002 |
| WO | WO02/083154 | 10/2002 |
| WO | WO03/043586 | 5/2003 |
| WO | WO03/092659 | 11/2003 |
| WO | WO03/105780 | 12/2003 |
| WO | WO2004/006897 | 1/2004 |
| WO | WO2004/012690 | 2/2004 |
| WO | WO2004/030659 | 4/2004 |
| WO | WO2004/039960 | 5/2004 |
| WO | WO2004/041991 | 5/2004 |
| WO | WO2004/060351 | 7/2004 |
| WO | WO2004/071521 | 8/2004 |

(56) References Cited

FOREIGN PATENT DOCUMENTS

| WO | WO2004/082660 | 9/2004 |
| --- | --- | --- |
| WO | WO2004/112695 | 12/2004 |
| WO | WO2004/112696 | 12/2004 |
| WO | WO2005/007080 | 1/2005 |
| WO | WO2005/011636 | 2/2005 |
| WO | WO2005/025541 | 3/2005 |
| WO | WO2005/025550 | 3/2005 |
| WO | WO2005/055976 | 6/2005 |
| WO | WO2005/084644 | 9/2005 |
| WO | WO2005/115330 | 12/2005 |
| WO | WO2005/117962 | 12/2005 |
| WO | WO2006/003504 | 1/2006 |
| WO | WO2006/036617 | 4/2006 |
| WO | WO2007/027918 | 3/2007 |
| WO | WO2008/011086 | 1/2008 |
| WO | WO2008/092057 | 7/2008 |
| WO | WO2008/101173 | 8/2008 |
| WO | WO2009/046440 | 4/2009 |
| WO | WO 2009091416 A2 | 7/2009 |
| WO | WO2010/102066 | 9/2010 |
| WO | WO2010/132827 | 11/2010 |

OTHER PUBLICATIONS

Chemicalland21 (http://www.chemicalland21.com/industrialchem/solalc/ETHYL%20ACETATE.htm) searched on Apr. 20, 2013.

Grenha et al., "Microencapsulated chitosan nanoparticles for lung protein delivery," *European Journal of Pharmaceutical Sciences*, vol. 25, Issues 4-5, pp. 427-437 (Jul.-Aug. 2005).

International Search Report and Written Opinion, dated Feb. 17, 2011, issued in related International Application No. PCT/US2010/027930. 13 pages.

International Search Report and Written Opinion, dated Feb. 24, 2012, issued in related International Application No. PCT/US2011/050218. 11 pages.

International Search Report and Written Opinion, dated Feb. 24, 2012 issued in related International Application No. PCT/US2011/050222, 12 pages.

International Search Report and Written Opinion, dated Feb. 17, 2012, issued in related International Application No. PCT/US2011/052819. 9 pages.

Kawashima et al., "A New Powder Design Method to Improve Inhalation Efficiency of Pranlukast Hydrate Dry Powder Aerosols by Surface Modification with Hydroxypropylmethylcellulose Phthalate Nanospheres," *Pharmaceutical Research*, vol. 15, No. 11, pp. 1748-752 (Nov. 1998).

Rasenack et al., "Micronization of Anti-Inflammatory Drugs for Pulmonary Delivery by a Controlled Crystallization Process," *Journal of Pharmaceutical Sciences*, vol. 92, No. 1, pp. 35-44 (Jan. 2003).

Sham et al., "Formulation and characterization of spray-dried powders containing nanoparticles for aerosol delivery to the lung," *International Journal of Pharmaceutics*, vol. 269, Issue 2, pp. 457-467 (Jan. 2004).

Steckel et al., "In-situ-micronization of disodium cromoglycate for pulmonary delivery," *European Journal of Pharmaceutics and Biopharmaceutics*, vol. 55, No. 2, pp. 173-180 (Mar. 2003).

Steckel et al., "In vitro characterization of jet-milled and in-situ-micronized fluticasone-17-propionate," *International Journal of Pharmaceutics*, vol. 258, Issues 1-2, pp. 65-75 (Jun. 2003).

The product book, "Ezetimibe": [retrieved on Aug. 23, 2014 from the website http://www.scbt.com/datasheet-205690-ezetimibe.html].

US 5,849,884, 12/1998, Woiszwillo et al. (withdrawn)

SPRAY-DRYING APPARATUS AND METHODS OF USING THE SAME

CROSS REFERENCE TO RELATED APPLICATIONS

This application is a continuation of U.S. application Ser. No. 13/820,483, filed Mar. 1, 2013, which is the U.S. National Stage of International Application No. PCT/US2011/050222, filed Sep. 1, 2011, published in English under PCT Article 21(2), which claims the benefit of and priority to U.S. Provisional Patent Application No. 61/380,103 filed on Sep. 3, 2010. The prior applications are each incorporated by reference herein in its entirety.

FIELD

The present disclosure is directed to novel spray-drying apparatuses and methods of using the same.

BACKGROUND

The use of spray drying to produce powders from fluid feed stocks is well known, with applications ranging from powdered milk to bulk chemicals and pharmaceuticals. A typical spray-drying apparatus comprises a drying chamber, an atomizing means for atomizing a solvent-containing feed into the drying chamber, a drying gas that flows into the drying chamber to remove solvent from the atomized solvent-containing feed, and a product collection means located downstream of the drying chamber.

SUMMARY

In one embodiment, a spray-drying apparatus is provided. The apparatus includes a drying-gas conduit and a drying chamber having a first end, second end, and at least one side wall extending between the first and second ends to define an interior of the drying chamber having a central axis. A nozzle can be positioned at the first end of the drying chamber. The nozzle can be configured to atomize a liquid and spray the atomized liquid into the interior of the drying chamber. The drying-gas conduit is in fluid communication with the drying chamber, and is configured to direct a flow of drying gas in the drying chamber. At least a portion of the at least one side wall that surrounds the nozzle at the first end of the drying chamber extends away from the center axis at a first angle relative to the center axis, the first angle being at least 5° but less than 45°. A ratio of the length between the first and second ends to a maximum width between opposing internal surfaces of the interior of the drying chamber is at least 5 to 1.

In one embodiment, a spray-drying apparatus is provided. The apparatus includes a drying-gas conduit and a drying chamber having a first end, second end, and at least one side wall extending between the first and second ends to define an interior of the drying chamber having a central axis. A nozzle can be positioned at the first end of the drying chamber. The nozzle can be configured to atomize a liquid and spray the atomized liquid into the interior of the drying chamber. The drying-gas conduit is in fluid communication with the drying chamber, and is configured to direct a flow of drying gas to enter the drying chamber in substantially parallel flow. At least a portion of the at least one side wall that surrounds the nozzle at the first end of the drying chamber extends away from the center axis at a first angle relative to the center axis, the first angle being at least 5° but less than 45°. A ratio of the length between the first and second ends to a maximum width between opposing internal surfaces of the interior of the drying chamber is at least 5 to 1.

In certain embodiments, the drying gas entering the drying chamber satisfies at least one of (a) the velocity vector of the drying gas averaged over the opposing internal surfaces of the interior of the drying chamber is essentially parallel to the center axis of the drying chamber and is substantially towards the second end of the drying chamber; and (b) circulation cells near the first end of the drying chamber in the vicinity of the nozzle have diameters of less than 20% of the maximum width between opposing internal surfaces of the interior of the drying chamber. In certain embodiments, the drying gas entering the drying chamber satisfies both (a) and (b).

In certain embodiments, the walls of the drying gas conduit are generally parallel to the walls of the drying chamber.

In certain embodiments, the ratio of the length between the first and second ends to a maximum width between opposing internal surfaces of the interior of the drying chamber is at least 6 to 1.

In certain embodiments, a ratio of the maximum width to the width at the second end of the drying chamber interior is less than 3 to 1.

In certain embodiments, the nozzle is configured to atomize a liquid into the drying chamber at a maximum spray pattern angle relative to the center axis of less than 45°.

In certain embodiments, the first angle is at least 5° but less than 30° relative to the center axis. In certain embodiments, the nozzle is configured to atomize a liquid into the drying chamber at a maximum spray pattern angle relative to the center axis of less than 30°.

In certain embodiments, the first angle is at least 5° but less than 20° relative to the center axis. In certain embodiments, the nozzle is configured to atomize a liquid into the drying chamber at a maximum spray pattern angle relative to the center axis of less than 20°. In certain embodiments, the first angle is at least 10° but less than 20° relative to the center axis.

In certain embodiments, the at least one side wall of the drying chamber further comprises a second tapered portion at the second end, and the second tapered portion is narrowest at the second end and widest at a distance furthest from the second end.

In certain embodiments, the at least one side wall of the drying chamber further comprises a cylindrical portion of generally constant width located between the first and second tapered portions. In certain embodiments, the at least one side wall of the drying chamber has a generally circular cross section at each point along the center axis between the first end and the second end.

In certain embodiments, the atomized liquid comprises at least one active agent and at least one excipient. In certain embodiments, the atomized liquid comprises an active agent and at least one excipient in a solvent.

In certain embodiments, the atomized liquid can form particles that have a mass median aerodynamic diameter of less than 50 microns. In some embodiments, the particles have a mass median aerodynamic diameter of less than 20 microns. In some embodiments the particles can have a mass median aerodynamic diameter of less than 10 microns. In yet other embodiments, the particles can have a mass median aerodynamic diameter of less than 5 microns. In some embodiments, the particles can be inhalable particles.

In another embodiment, a method of spray drying is provided. The method can include forming a plurality of particles by atomizing a spray solution using a nozzle positioned at the first end of the drying chamber. The drying chamber comprises a second end and at least one side wall extending between the first and second ends to define an interior of the drying chamber having a center axis. At least a portion of the at least one side wall that surrounds the nozzle at the first end of the drying chamber extends away from a center axis of the drying chamber at a first angle relative to the center axis. The first angle can be at least 5° but less than 45°. A ratio of the length between the first and second ends to a maximum width between opposing internal surfaces of the interior of the drying chamber is at least 5 to 1. The atomized spray solution is delivered into the drying chamber and a flow of drying gas is delivered into the drying chamber to at least partially dry the atomized spray solution to form a plurality of particles. The plurality of particles are directed out of the drying chamber.

In another embodiment, a method of spray drying is provided. The method can include forming a plurality of particles by atomizing a spray solution using a nozzle positioned at the first end of the drying chamber. The drying chamber comprises a second end and at least one side wall extending between the first and second ends to define an interior of the drying chamber having a center axis. At least a portion of the at least one side wall that surrounds the nozzle at the first end of the drying chamber extends away from a center axis of the drying chamber at a first angle relative to the center axis. The first angle can be at least 5° but less than 45°. A ratio of the length between the first and second ends to a maximum width between opposing internal surfaces of the interior of the drying chamber is at least 5 to 1. The atomized spray solution is delivered into the drying chamber and a flow of drying gas is delivered into the drying chamber in substantially parallel flow to at least partially dry the atomized spray solution to form a plurality of particles. The plurality of particles are directed out of the drying chamber.

In some embodiments, the atomized spray solution can be delivered into the drying chamber at a maximum spray pattern angle relative to the center axis of less than 45°. In some embodiments, the atomized spray solution is delivered into the drying chamber at a maximum spray pattern angle relative to the center axis of less than 30°. In some embodiments, the atomized spray solution is delivered into the drying chamber at a maximum spray pattern angle relative to the center axis of less than 20°.

In some embodiments, the first angle is at least 5° but less than 30° relative to the center axis. In other embodiments, the first angle is at least 5° but less than 20° relative to the center axis.

In other embodiments, the spray solution comprises at least one excipient. In yet other embodiments, the particles formed in the drying chamber have a mass median aerodynamic diameter of less than 10 microns. In some embodiments, the particles can be inhalable particles.

In other embodiments, the particles can have a mean particle residence time of less than 10 seconds, or in other embodiments, less than 8 seconds, less than 5 seconds, or less than 3 seconds.

The foregoing and other objects, features, and advantages of the disclosed embodiments will become more apparent from the following detailed description, which proceeds with reference to the accompanying figures.

DETAILED DESCRIPTION

Figure 1:
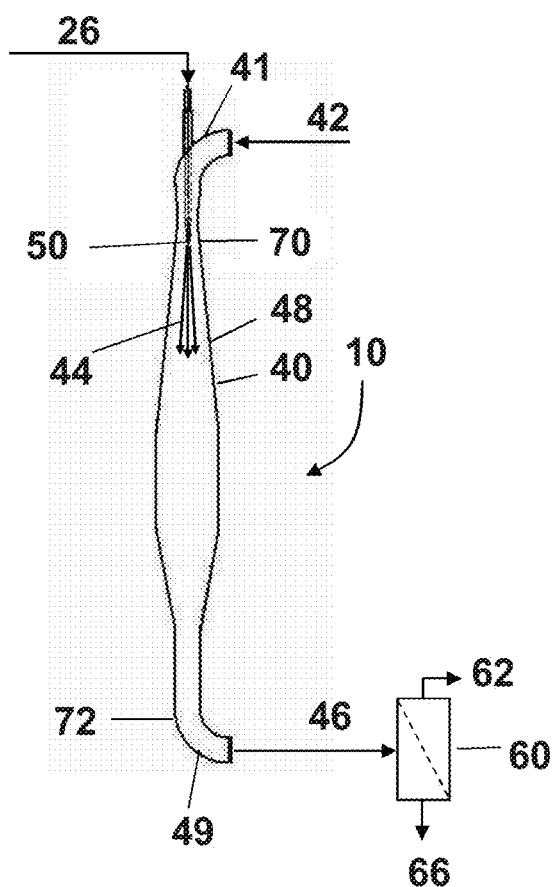
FIG. 1 is a schematic view of a spray-drying apparatus.

Various embodiments of spray-drying apparatuses and their methods of use are disclosed herein. The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Unless otherwise indicated, all numbers expressing quantities of ingredients, properties such as molecular weight, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Conventional spray-drying apparatuses require a drying chamber of a relatively large diameter to provide the desired throughput of fluid feed stock. These large diameter drying chambers can be relatively expensive to manufacture and operate due to increased air handling, utility, and construction costs. Also, the combination of the large drying chamber and the manner in which drying gas enters the chamber results in non-parallel gas flow with large circulation cells. Such gas flow patterns can carry particles to the chamber wall before complete drying, can lead to long residence times, and can even result in particles contacting hot gas and hot metal surfaces near the drying gas entrance.

In addition, particle residence times in these large drying chambers can be quite long and variable, causing at least some particles to be exposed to elevated temperatures and elevated solvent concentrations, which can damage or reduce the efficacies of active agents in the particles. The particle residence time distributions in large drying chambers can also be quite broad, leading to large differences in particle properties within a single batch of spray dried powder. An apparatus with a smaller diameter and with substantially parallel flow in the vicinity of the spray nozzle results in shorter particle residence times, and a much narrower particle residence time distribution, resulting in more uniform particle properties.

The collection efficiencies of conventional larger diameter drying chambers can also be relatively poor, due to the lower pressures maintained in these larger diameter drying chambers, especially when spray drying particles with relatively small diameters, such as those with diameters of 10 μm or less. In addition, the larger diameter of conventional spray-drying apparatuses leads to a high surface area and high surface area to volume ratios, and a corresponding high heat loss. An apparatus with a smaller diameter and correspondingly smaller surface area and/or surface to volume ratio, can reduce heat loss, making the spray drying process more efficient. The larger diameter of conventional spray-drying apparatuses leads to large drying-chamber volumes, making operation at elevated pressures expensive due to the increased strength required to maintain a large volume under elevated pressure. By using a relatively small volume drying chamber, higher pressures can be achieved within the drying chamber, resulting in lower capital costs, and higher particle collection efficiencies. Conventional spray drying apparatuses also require a large room to accommodate all the equipment. By using a small volume drying chamber, the room space required is greatly reduced, further reducing capital costs required for installation and operation of the spray dryer. The larger diameters and higher surface areas of conventional spray-drying apparatuses also leads to large amounts of cleaning agents required after each use and when changing from one product to another. Thus, a smaller diameter dryer with a smaller surface area can reduce the amount of cleaning agents required by the spray-drying system.

Accordingly, there is a need for an improved spray-drying apparatus design that results in the production of spray-dried solids with lower equipment costs, exposure of particles to lower maximum temperatures, shorter duration of exposure to elevated temperatures, more uniform drying conditions for all droplets and particles, and improved collection efficiency.

In particular, the combination of (1) a smaller volume, larger aspect ratio drying chamber, (2) atomization of the liquid to be dried such that the droplets are directed parallel to or away from the drying chamber walls, (3) introduction of the drying gas such that it enters the drying chamber in a uniform flow pattern that is substantially parallel to the center axis of the drying chamber, and (4) construction of the drying gas conduit and drying chamber such that there are few gas circulation cells, results in extremely efficient drying, uniform and relatively short exposure of droplets and particles to heat and solvent vapors, and high product recovery.

An embodiment of the disclosed spray-drying apparatus is shown in FIG. 1. Although the following embodiments illustrate spray-drying apparatuses that are generally circular in cross section, it should be understood that the apparatus can take any other cross-sectional shapes suitable for spray drying a spray solution, including, for example, square, rectangular, and octagonal shapes, among others.

As shown in FIG. 1, spray-drying apparatus 10 can comprise a drying chamber 40, a nozzle 50, and a particle collection member 60. In one embodiment, the spray-drying apparatus 10 can be utilized as follows. A spray solution 26 can be formed by mixing a solute with a solvent. In one embodiment, the spray solution may be stored in a feed tank (not shown in FIG. 1). The spray solution may be kept homogenous using a mixing means (also not shown in FIG. 1). In another embodiment, the spray solution may be prepared continuously.

As used herein, the term "spray solution" means a composition comprising a solute and a solvent. The term "solute" means a material that is desired to be spray dried. In one embodiment, the solute comprises at least one active agent. In another embodiment, the solute comprises at least one excipient. In still another embodiment, the solute comprises a mixture of at least one active agent and at least one excipient.

In one embodiment, the spray solution 26 comprises an active agent and a solvent. In another embodiment, the spray solution 26 comprises an excipient and a solvent. In still another embodiment, the spray solution 26 comprises an active agent, at least one excipient, and a solvent. The spray solution 26 can include, for example, mixtures, solutions, and/or suspensions. For example, in one embodiment, the active agent can be dissolved in the solvent. In another embodiment, a portion of the active agent can be suspended or not dissolved in the solvent. In another embodiment, the active agent can be dissolved in the solvent, while a portion of an excipient is dissolved in the solvent. In another embodiment, a portion of the active agent, a portion of an excipient, or a portion of both an active agent and an excipient can be suspended or not dissolved in the solvent.

In one embodiment, the spray solution 26 consists essentially of an active agent, at least one excipient, and a solvent. In still another embodiment, the spray solution consists of an active agent, at least one excipient, and a solvent. In yet another embodiment, the spray solution consists of particles of active agent suspended in a solution of at least one excipient dissolved in the solvent. In yet another embodiment, the spray solution also contains particles of one or more excipients suspended in the solution. It will be recognized that in such spray solutions, a portion of the active agent and the one or more excipients may dissolve up to their solubility limits at the temperature of the spray solution.

As used herein, "active agent" means a drug, medicament, pharmaceutical, therapeutic agent, nutraceutical, nutrient, or other compound. The active agent may be a "small molecule," generally having a molecular weight of 2000 Daltons or less. The active agent may also be a "biological active." Biological actives include proteins, antibodies, antibody fragments, peptides, oligoneucleotides, vaccines, and various derivatives of such materials. In one embodiment, the active agent is a small molecule. In another embodiment, the active agent is a biological active. In still another embodiment, the active agent is a mixture of a small molecule and a biological active. In yet another embodiment, the compositions made by certain of the disclosed processes comprise two or more active agents.

As used herein, the term "solvent" means water or an organic compound that can be used to dissolve or suspend the solute. In one embodiment, the solvent is volatile, having an ambient-pressure boiling point of 150° C. or less. In another embodiment, the solvent has an ambient-pressure boiling point of 100° C. or less. Suitable solvents can include water; alcohols such as methanol, ethanol, n-propanol, isopropanol, and butanol; ketones such as acetone, methyl ethyl ketone and methyl isobutyl ketone; esters such as ethyl acetate and propyl acetate; and various other solvents, such as tetrahydrofuran, acetonitrile, methylene chloride, toluene, and 1,1,1- trichloroethane. Lower volatility solvents such as dimethylacetamide or dimethylsulfoxide can also be used, generally in combination with a volatile solvent. Mixtures of solvents, such as 50% methanol and 50% acetone, can also be used, as can mixtures with water.

As used herein, the term "excipient" means a substance that may be beneficial to include in a composition with an active agent. The term "excipient" includes inert substances as well as functional excipients that may result in beneficial properties of the composition. Exemplary excipients include but are not limited to polymers, sugars, salts, buffers, fats, fillers, disintegrating agents, binders, surfactants, high surface area substrates, flavorants, carriers, matrix materials, and so forth.

The spray solution can be delivered to a nozzle 50 via a pump or other delivery device (not shown). Nozzle 50 atomizes the spray solution into the drying chamber in the form of droplets 44. Drying gas 42 flows through a drying-gas conduit 41, which is in fluid communication with the first end 70 of drying chamber 40. In one embodiment, the first end 70 of the drying chamber is located at the position where the spray solution exits the nozzle 50. In one embodiment, the drying-gas conduit 41 is configured to allow the drying gas 42 to enter the drying chamber 40 with substantially parallel flow. As used herein, "substantially parallel flow" means that the flow of drying gas 42 entering the drying chamber satisfies at least one of the following two conditions. First, the velocity vector of the drying gas 42 averaged over the cross-section of the first end 70 of the drying chamber 40 is essentially parallel to the center axis of drying chamber 40 and is substantially towards the second end 72 of drying chamber 40. Second, any circulation cells near the first end 70 of the drying chamber 40 in the vicinity of nozzle 50 are small, with the diameter of the circulation cells being less than 20% of the maximum width between opposing internal surfaces of the interior of the drying chamber 40. As used herein, "essentially parallel" means that the velocity vector averaged over the cross-section of the first end 70 of the drying chamber 40 has a direction that ranges between the center axis of the drying chamber and the angle formed by the walls 48 of the drying chamber 40. In one embodiment, the drying gas entering the drying chamber meets both of these conditions.

In another embodiment, the drying gas streamlines, defined as the local gas velocity vectors, are essentially all directed from the first end 70 of the drying chamber 40 toward the second end 72 of the drying chamber. In addition, these drying gas streamlines have vectors that are between the vector defined by the center line of the drying chamber 40 and the vectors defined by the walls 48 of the drying chamber.

To achieve substantially parallel flow, the drying-gas conduit 41 and first end 70 should generally be free from sharp surfaces or protrusions that could disrupt the flow of the drying gas 42. In addition, the walls of the drying gas conduit 41 and the drying chamber 40 should be generally parallel to each other where the drying gas conduit 41 is coupled to the drying chamber 40, particularly when it is coupled in the vicinity of the nozzle. As used in this context herein, "generally parallel" means that an angle formed between the walls of the gas conduit and drying chamber relative to the center axis of the drying chamber 40 is less than 45°. In one embodiment, the drying-gas conduit 41 contains at least one flow straightener, such as a mesh, screen, or perforated plate that results in substantially parallel flow when the drying gas 42 enters the drying chamber 40. In another embodiment, the drying gas conduit 41 is smooth, having a radius of curvature that is at least twice the width between opposing side walls at the first end 70 of the drying chamber 40.

The drying gas 42 is combined with the droplets 44 in the drying chamber 40. In the drying chamber 40, at least a portion of the solvent is removed from the droplets 44 to form an exiting fluid 46 comprising evaporated solvent and drying gas 62 and a plurality of at least partially dried particles 66. The term "exiting fluid" refers to any fluids, particles, or combinations of fluids and particles that exit the drying chamber 40.

The exiting fluid 46 exits the drying chamber at the second end 72 through exit conduit 49, and can be directed to a particle collection member 60. Suitable particle collection members include cyclones, filters, electrostatic particle collectors, and the like. In the particle collection member 60, the evaporated solvent and drying gas 62 can be separated from the plurality of particles 66, allowing for collection of the particles 66.

Figure 3:
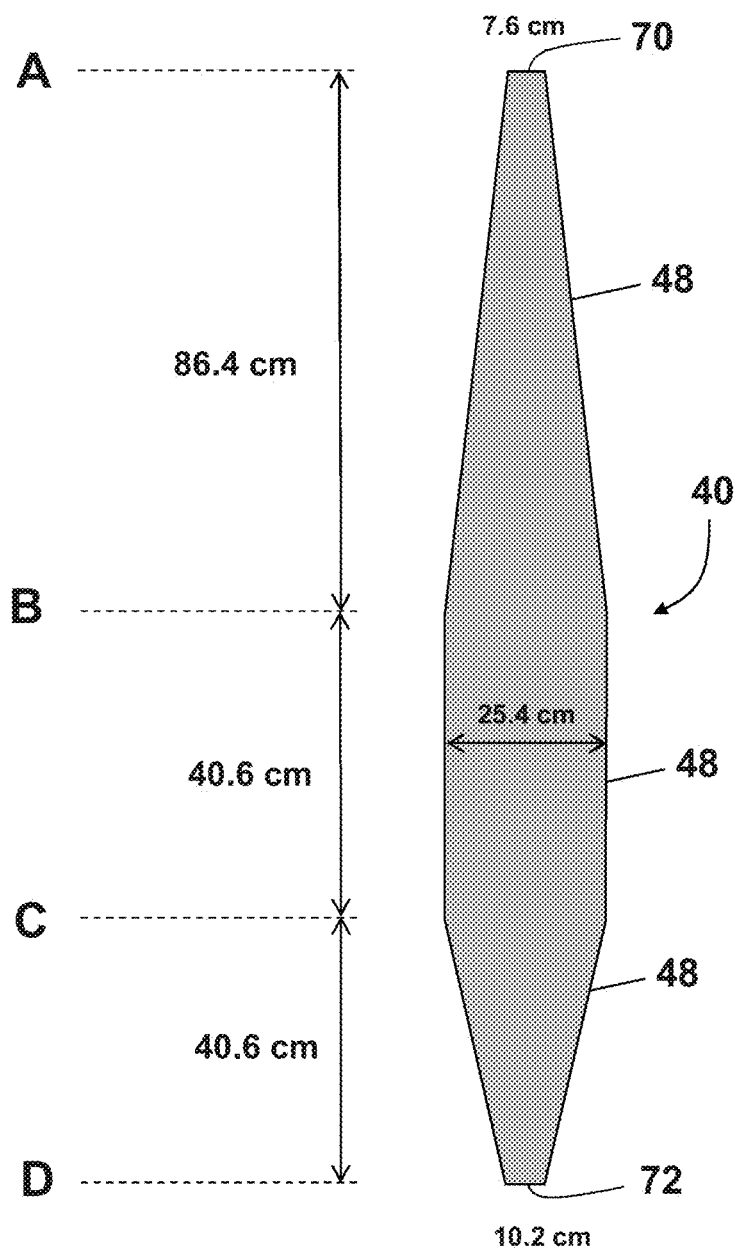
FIG. 3 is a side view of an embodiment of the drying chamber of a spray-drying apparatus.

As shown in FIGS. 1 and 3, drying chamber 40 has a first end 70 and a second end 72. First end 70 can be an inlet for receiving the nozzle and can be coupled to the drying gas conduit 41 for receiving the drying gas 42. Second end 72 can be an outlet that can be coupled to an exit conduit 49, and then to a particle collection member 60 or other such device to receive and collect the particles as they exit drying chamber 40. The interior volume of drying chamber 40 can be defined by one or more side walls 48 that extend between first and second ends 70, 72. If drying chamber 40 comprises a single integral structure, a single side wall 48 can extend from first end 70 to second end 72. Alternatively, drying chamber 40 can be formed of sections that include multiple side walls 48 that are coupled together to form a single drying chamber.

In one embodiment, the first end 70 of the drying chamber 40 is located where the spray solution exits the nozzle 50 via one or more outlets in the nozzle 50, while the second end 72 is located where the exit conduit 49 starts.

Figure 2:
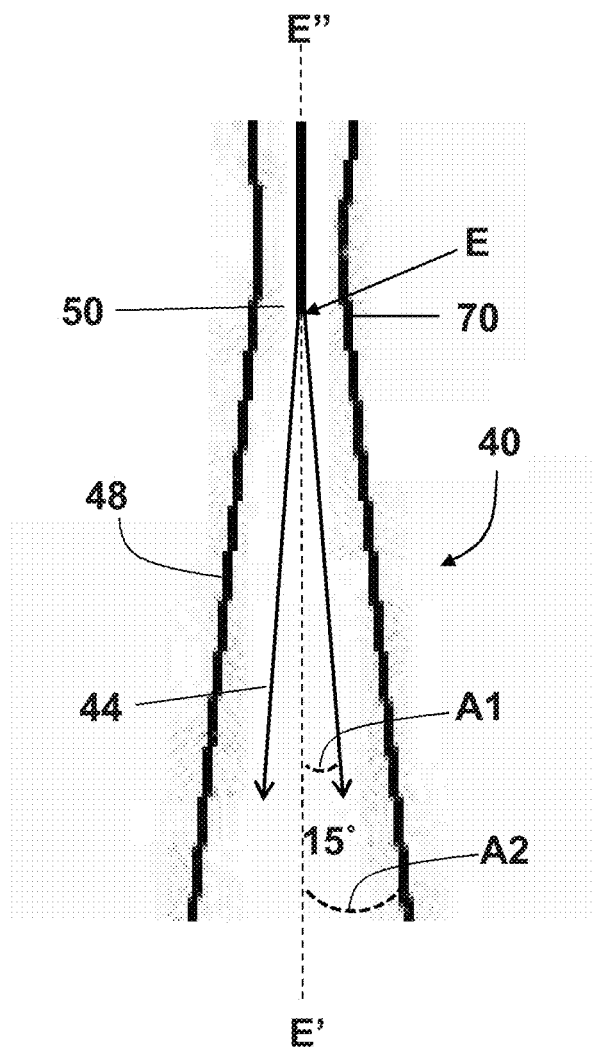
FIG. 2 is an enlarged cross-sectional view of one embodiment of a drying chamber.

FIG. 2 shows an enlarged cross-sectional view of an embodiment of the first end 70 of drying chamber 40. Nozzle 50 can be centrally positioned at first end 70 of drying chamber 40 along the center axis of the drying chamber E-E', which generally extends longitudinally along the center axis of drying chamber 40. Nozzle 50 can have a spray pattern such that droplets 44 are directed out of nozzle 50 at a maximum spray angle A1. Angle A1 can be equal to an angle A2 formed between center line E-E' and a side wall 48 of drying chamber 40 that is adjacent to or in the vicinity of nozzle 50. In one embodiment, angles A1 and A2 are generally equal, that is, within about 5 degrees of one another. Drying gas 42 enters the drying chamber 40 via drying gas conduit 41 with an exit centerline E-E". In one embodiment, drying gas conduit 41 exit centerline E-E" is parallel to the center axis of the drying chamber E-E'. In another embodiment, E-E" and E-E' are approximately coincident.

Generally, the temperature and flow rate of the drying gas should be chosen so that the droplets of spray solution are dry enough by the time they reach the wall of the apparatus that, at least on the particle surface, they are essentially solid, form a fine powder, and do not stick to the apparatus wall. The actual length of time to achieve this level of dryness depends on the size of the droplets and the conditions at which the process is operated. In conventional systems, droplets exit the nozzle and are directed on a range of trajectories such that many of their trajectories are towards the side walls. In addition to increasing residence time, directing droplets towards the side walls requires that the distance from the nozzle to the side wall be sufficiently large so that the ejected droplets have enough time to dry, at least on the surface of the droplets, before contacting the side wall. By providing a nozzle and angled side wall as shown in FIG. 1, however, the width (e.g., diameter) of the spray-drying apparatus can be reduced since the droplets are directed generally parallel to the side wall. Accordingly, by forming angles A1 and A2 generally equal to one another, droplets can be provided with sufficient time to dry, without requiring a wide drying chamber.

One of ordinary skill will understand that the required length of the angled side wall will be a function of (1) the droplet diameter, (2) the droplet velocity, (3) the drying gas velocity, and (4) the time for the droplet to become sufficiently dry on the surface so that the particle doesn't stick to the walls of the drying chamber. Generally, larger droplet diameters will require longer lengths of the angled side wall to ensure the droplet is sufficiently dry before contacting the interior walls of the drying chamber.

To the extent that one of angles A1 and A2 are different, angle A1 is somewhat smaller than angle A2 to reduce the chance that atomized spray solution or particles will contact the side wall of the drying chamber.

Accordingly, if the maximum spray angle A1 does not exceed the angle A2 formed by side wall 48, droplets or particles exiting nozzle 50 are directed away from or parallel to the side wall and not towards side wall 48. To substantially direct the droplets in a direction generally parallel to the side wall of the drying chamber, angle A1 is 45 degrees or less. Angle A1 can also be 40 degrees or less, 35 degrees or less, 30 degrees or less, 25 degrees or less, 20 degrees or less, 15 degrees or less, 10 degrees or less, or 5 degrees or less.

As shown in FIGS. 1 and 2, droplets ejected from nozzle 50 with a maximum spray pattern of 45 degrees or less can be directed along a path that generally does not intersect with side wall 48 that is adjacent to or in the vicinity of nozzle 50. In the illustrated embodiment of FIG. 2, angle A1 is 15 degrees.

As described above, in one embodiment, angle A2 is substantially equal to angle A1. Thus, if angle A2 is equal to 30 degrees and nozzle 50 has a maximum spray angle A1 that is equal to or less than 30 degrees, droplets 44 are directed away from or along (i.e., parallel to) the inner surface of side wall 48 and generally prevented from contacting the side wall of the drying chamber. In the illustrated embodiment of FIG. 2, angle A1 is 15 degrees and angle A2 is substantially equal to A1 (i.e., angle A2 is about 15 degrees).

FIG. 3 shows a cross-section of an embodiment of drying chamber 40. Position A is the inlet (first end 70) and Position D is the outlet (second end 72) of drying chamber 40. As shown in other embodiments, a nozzle can be located at or near position A. In this embodiment, the drying chamber includes three main sections. Section A-B is an expanding tapered section, Section B-C is a straight section, and Section C-D is a contracting tapered section. In one embodiment, the expanding tapered section A-B can be 75-100 cm long and can be narrowest at the inlet end (Position A) and widest at a position furthest from the inlet end. The straight section B-C can be 25-50 cm long and can have a substantially constant width along its length. The contracting tapered section C-D can be 25-50 cm long and can be narrowest at the outlet end (second end 72, Position D) and widest at a position furthest from the second end 72. Accordingly, in one embodiment, a total length of the drying chamber (i.e., the length of section A-B+the length of section B-C+the length of section C-D) can vary from 125 cm to 200 cm. One of ordinary skill will understand that drying chambers with other lengths and widths can be constructed and be within the scope of the invention, and the invention is not limited to the lengths and widths described above.

The three sections can be separate side walls 48 that are coupled or connected together in any conventional manner (e.g., mechanically and/or chemically). Alternatively, the three sections can be integrally formed of a single side wall member.

In the embodiment shown in FIG. 3, the width of the apparatus is 25.4 cm (10 inches). The width at any point along the length of the drying chamber is the distance between opposing internal surfaces of the side wall(s). Thus, the ratio of the length to the maximum width of the drying chamber is at least 5 to 1 (e.g., the length is at least 125 cm if the width is 25 cm) and can even be greater than 6 to 1. In one embodiment, the ratio of the length to the maximum width of the drying chamber can be even greater, such as 10 to 1, or more. By providing a drying chamber that has a length that is significantly greater than its width, residence time in the drying chamber can be greatly reduced. Instead of being captured and recirculated within the drying chamber, droplets or particles ejected from the nozzle are directed towards the second end 72 and out of the drying chamber 40 through exit conduit 49. The substantial length (relative to the width) provides enough time for the droplets or particles to be sufficiently dried before exiting the drying chamber.

In one embodiment, section A-B can be 86.4 cm (34 inches) long and tapers from 7.6 cm (3 inches) wide at Position A to 25.4 cm (10 inches) wide at Position B. The straight section B-C can be 40.6 cm (16 inches) long. The contracting tapered section C-D can be 40.6 cm (16 inches) long and tapers from 25.4 cm (10 inches) wide at Position C to 10.2 cm (4 inches) wide at Position D. Thus, in this specific implementation, the ratio of the length to the maximum width of the drying chamber is 6.6 to 1 (i.e., 167.6 cm to 25.4 cm).

In addition, in the above embodiment, although the second end 72 has an opening with a smaller diameter (10 cm) than the diameter of the maximum width between opposing surfaces of the interior of the drying chamber (25 cm), the ratio of the maximum width between opposing surfaces of the interior of the drying chamber to the diameter at the second end of the drying chamber interior is less than 6 to 1. In other embodiments, the ratio of the maximum width between opposing surfaces of the interior of the drying chamber to the diameter at the second end of the drying chamber interior may be less than 5 to 1, less than 4 to 1, less than 3 to 1, or even less than 2.5 to 1. Generally, to aid in the collection of particles, the ratio of the maximum width between opposing surfaces of the interior of the drying chamber to the diameter at the second end of the drying chamber interior should be greater than 1.1 to 1.

In one embodiment of FIG. 3, the apparatus has a generally cylindrical shape. The first end of the drying chamber (70) is located at Position A. The second end of the drying chamber (72) is located at Position D. The cylindrical walls of the drying chamber (48) define an interior of the drying chamber having a center axis. The nozzle is located at or near the first end (70) of the drying chamber at Position A. A portion of the cylindrical walls of the drying chamber (48) extends away from the center axis at a first angel relative to the center axis (Section A-B). The drying chamber further comprises a cylindrical portion of generally constant width at Section B-C. The drying chamber further comprises a second tapered portion (Section C-D) at the second end (72) that is narrowest at the second end (72, Position D), and widest at Position C. The ratio of the length between the first end (70) and the second end (72) (that is, the length between Positions A and D) to the maximum width between opposing internal surfaces of the interior of the drying chamber (that is, at Position B) is at least 5 to 1. In one embodiment, a ratio of the maximum width (at Position B) to the width at the second end (72) of the drying chamber (at Position D) is less than 3 to 1.

In one embodiment, the plurality of particles produced in the apparatuses disclosed herein are inhalable particles that can be inhaled by a subject (e.g., human or animal). As used herein, the term "inhalation" refers to delivery to a subject through the mouth or nose. In one embodiment, the spray-dried particles are delivered to the "upper airways." The term "upper airways" refers to delivery to nasal, oral, pharyngeal, and laryngeal passages, including the nose, mouth, nasopharynx, oropharynx, and larynx. In another embodiment, the spray-dried particles are delivered to the "lower airways." The term "lower airways" refers to delivery to the trachea, bronchi, bronchioles, alveolar ducts, alveolar sacs, and alveoli.

In one embodiment, the particles have a mass median aerodynamic diameter (MMAD) of about 5 to 100 µm. In another embodiment, the particles have a MMAD of about 10 to 70 µm. Mass median aerodynamic diameter (MMAD) is the median aerodynamic diameter based on particle mass. In a sample of particles, 50% of the particles by weight will have an aerodynamic diameter greater than the MMAD, and 50% of the particles by weight will have an aerodynamic diameter smaller than the MMAD. In yet another embodiment, the particles have an average diameter of 50 µm, or even 40 µm, or 30 µm. In other embodiments, the particles can have an MMAD of less than about 20 µm, or even less than about 10 µm. In another embodiment, the particles have a MMAD ranging from 0.5 µm to 10 µm. In still another embodiment, the particles have a MMAD ranging from 1 µm to 5 µm.

In one embodiment, the particles are intended for inhalation and have a MMAD of 0.5 to 100 µm. In another embodiment, the particles are intended for inhalation and have a MMAD of 0.5 to 70 µm.

In one embodiment, the particles are intended for delivery to the upper airways, and have a MMAD of greater than 10 µm. In another embodiment, the particles are intended for delivery to the upper airways and have a MMAD of 10 to 100 µm, and wherein the weight fraction of particles having an aerodynamic diameter of less than 10 µm is less than 0.1. In another embodiment, the particles are intended for delivery to the upper airways and have a MMAD of 10 to 70 µm, and the weight fraction of particles having an aerodynamic diameter of less than 10 µm is less than 0.1.

In another embodiment, the particles are intended for delivery to the lower airways, and have a MMAD of less than 10 µm. In one embodiment, the particles are intended for delivery to the lower airways, and have a MMAD of 0.5 to 10 µm, and the weight fraction of particles having an aerodynamic diameter of greater than 10 µm is less than 0.1. In another embodiment, the particles are intended for delivery to the lower airways, and have a MMAD of 0.5 to 7 µm, and the weight fraction of particles having an aerodynamic diameter of greater than 7 µm is less than 0.1.

In some embodiments of inhalable particles, the active agent comprises a drug, medicament, pharmaceutical, therapeutic agent, nutraceutical, nutrient, or other compound suitable for treating, diagnosing, preventing, or otherwise affecting a particular physical condition or state of the patient.

Inhalable particles formed using the spray-drying apparatuses described herein can be dispersed in an inhalation device, such as an inhaler, without producing significant amounts of one or more of the following undesirable side effects when administered via inhalation to a subject: cough, emesis, toxic build-up in the lung, inflammation, reduced lung function. One measure of lung function is the $FEV_1$ (forced expiratory volume in one second) test, which measures the volume exhaled during the first second of a forced expiratory maneuver started from the level of total lung capacity.

In one embodiment, the concentration of solvent remaining in the particles when they are collected (that is, the concentration of residual solvent) is less than 10 wt % based on the total weight of the particles (i.e., the combined weight of the particle and solvent). In another embodiment, the concentration of residual solvent in the particles when they are collected is less than 5 wt %. In yet another embodiment, the concentration of residual solvent in the particles is less than 3 wt %. In another embodiment, a drying process subsequent to the spray-drying process may be used to remove residual solvent from the particles. Exemplary processes include tray drying, fluid-bed drying, vacuum drying, and other similar drying processes.

The drying gas may be virtually any gas, but to minimize the risk of fire or explosions due to ignition of flammable vapors, and to minimize undesirable oxidation of the active agent or other excipients, an inert gas such as nitrogen, nitrogen-enriched air, helium, or argon is utilized. The temperature of the drying gas at the gas inlet of apparatus 10 is typically from 20° to 300° C. The temperature of the product particles, drying gas, and evaporated solvent in the exiting fluid 46 typically ranges from 0° C. to 100° C.

By selecting a nozzle with a relatively small spray pattern angle (e.g., 30 degrees or less as measured relative to a central axis of the drying chamber) and providing a spray-drying chamber that generally encompasses only the space required to contain the spray plume contour of the nozzle, spray-dried solids can be produced satisfactorily with significantly smaller equipment. The smaller amount of space required for the spray-drying apparatuses disclosed herein relative to conventional spray-drying equipment, results in lower construction and utility costs (room size, air handling, etc.). In addition, the smaller size of the spray dryer allows it to be more easily enclosed in commercially available isolators, reducing operator exposure to highly potent compounds or aerosolized particles that can present an inhalation risk. This provides operators improved safety by further reducing potentially hazardous airborne particles.

The design also minimizes the amount of product buildup on the inside surfaces of the drying chamber, which improves production efficiency by reducing the amount of down time that is required for cleaning the drying chamber. By directing all particles generally parallel to the side walls—rather than directly towards the side walls as is the case in conventional spray-drying systems—few or none contact the side wall. Moreover, by directing a drying gas into the drying chamber in the manner shown in FIG. 6, even fewer particles contact the side walls since the drying gas further directs the droplets in a direction generally parallel to the side wall. Thus, by using the spray-drying apparatuses described herein, few, if any, droplets contact the side walls of the drying chamber, thereby reducing the amount of effort needed to clean the side walls.

In certain embodiments, the interior of the drying chamber has a volume that is 80 L or less, or even less than 70 L. In one embodiment, the drying chamber has a volume of between 55-65 L. By using a relatively small volume drying chamber, higher pressures can be achieved within the drying chamber. For example, a drying gas can be delivered into the drying chamber at 1200-1500 g/min, or even at 1300-1400 g/min. The temperature and type of gas can vary; however, temperatures of between 100 and 180 degrees Celsius are typical, with temperatures between 135 and 160 degrees Celsius being common. The small volume of the drying chamber in combination with the pressure of the drying gas results in high particle collection efficiencies at the second end of the drying chamber, as well as low residence times which can provide a number of benefits as described herein.

In one embodiment, the mean particle residence time of the spray-drying apparatuses disclosed herein can be less than 10 seconds. Shorter residence times can be obtained, and are sometimes desirable, such as less than 8 seconds, less than 5 seconds, or less than 3 seconds. In comparison, conventional spray-drying equipment often has residence times of 20 to 40 seconds for similar spray solution flow rates. The reduced particle residence time for the disclosed apparatuses reduces exposure to elevated drying gas temperatures that can cause degradation of active agents or excipients, allowing heat-sensitive materials to be spray dried. For example, compounds such as DNA, proteins, or antibodies that are not stable for long periods of time in a spray-drying chamber at high temperature and humidity, can be dried using the apparatuses disclosed herein due to the order of magnitude smaller residence time.

In addition to reducing the potential for degradation of active agents, shorter residence times also allow for the generation of a more consistent end product. Recirculation can cause widely varying residence times, which can result in large inconsistencies in particles as they exit the drying chamber. By reducing residence times and the related recirculation associated with longer residence times, spray-dried particles can be created with more consistent and predictable attributes, and with a narrower particle size distribution. Such consistency can be particularly important when spray-drying pharmaceutical compositions, such as the inhalable particles described herein. Thus, the spray-drying apparatuses disclosed herein can produce inhalable particles with a reduced variability in particle size and pharmacological activity. For example, Table 3 below illustrates the lower "Span" (a dimensionless parameter indicative of the uniformity of particle size distribution as described in more detail below) and improved fine particle fraction (FPF) of particles produced using a spray-drying apparatus as shown in FIG. 1 relative to conventional spray-drying systems.

Figure 8:
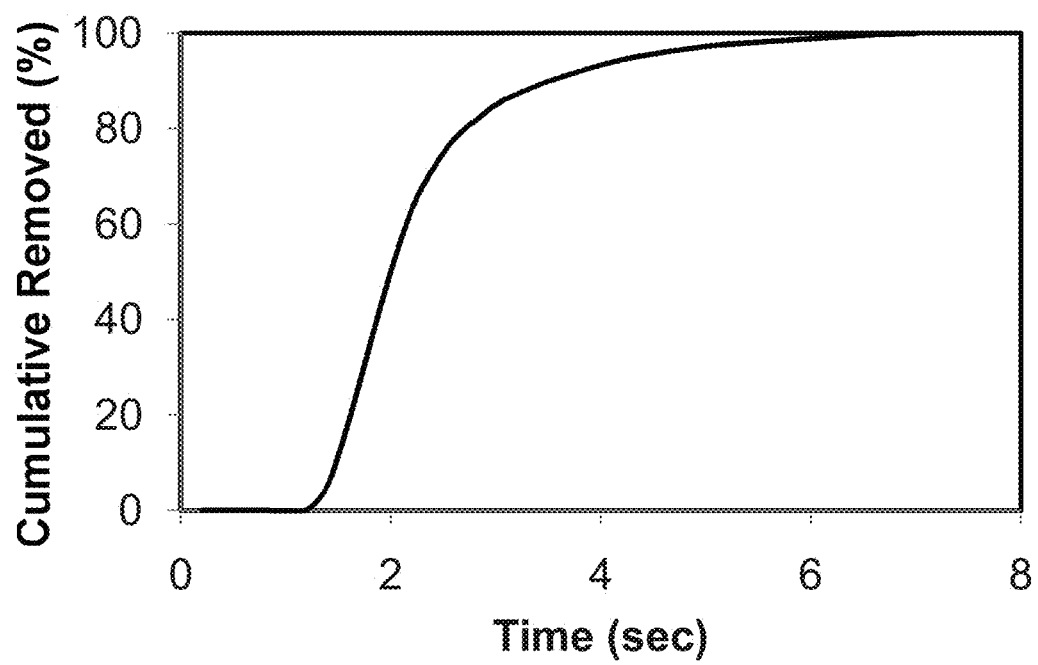
FIG. 8 is a graph illustrating particle residence time in a drying chamber of a spray-drying apparatus as described herein.

FIG. 8 illustrates particle residence time in a drying chamber using a spray-drying apparatus as shown in FIG. 1. In particular, FIG. 8 shows the cumulative percentage of particles removed from the drying chamber over time. As shown in FIG. 8, when actively directing atomized spray solution into the drying chamber, 50% of all particles can be removed from the drying chamber within 2 seconds, 80% of all particles can be removed from the drying chamber within 3 seconds, 90% of all particles can be removed from the drying chamber within 4 seconds, and more than 95% of all particles can be removed from the drying chamber within 6 seconds, and 100% of all particles can be removed from the drying chamber within 8 seconds.

An additional advantage of the spray-drying apparatuses disclosed herein is found in the collection of small particles. For spray-drying particles having diameters of less than 10 µm using conventional spray-drying equipment, collection efficiency can be particularly poor. As discussed above, the smaller volume chambers of the spray-drying apparatuses disclosed herein can allow a higher operating pressure, resulting in more efficient particle collection in a cyclone.

Figure 4:
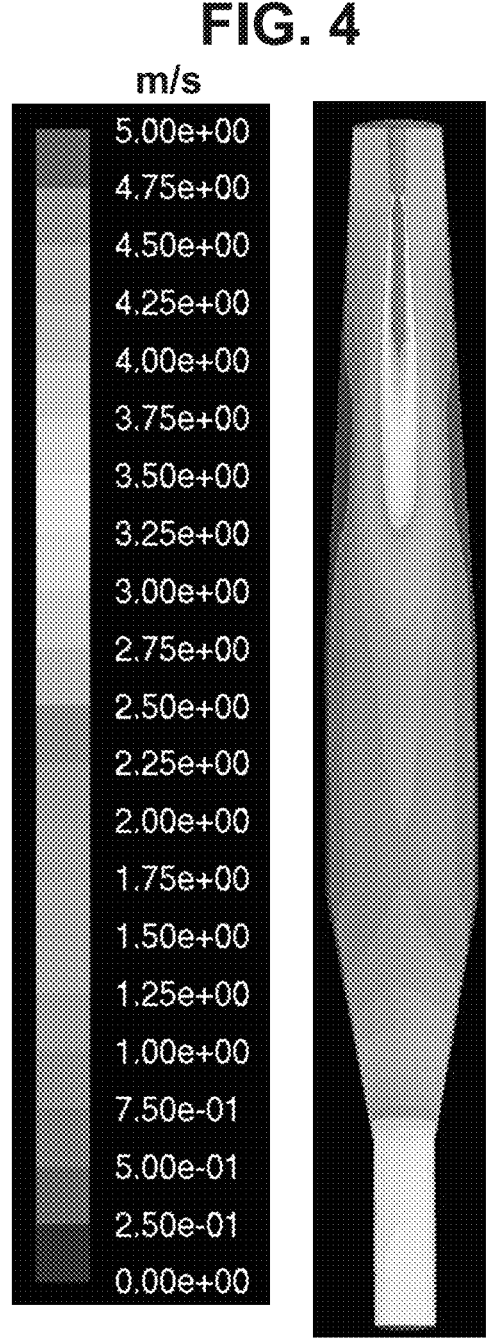
FIG. 4 shows velocity contours for one embodiment of the spray-drying apparatus.

FIG. 4 shows velocity contours for droplets and particles in one embodiment of the spray-drying chamber. The data in FIG. 4 illustrates that the droplets and particles move substantially parallel to the walls of the spray-drying chamber and contact with the walls by droplets or particles that have not been substantially dried is substantially prevented.

Figure 5:
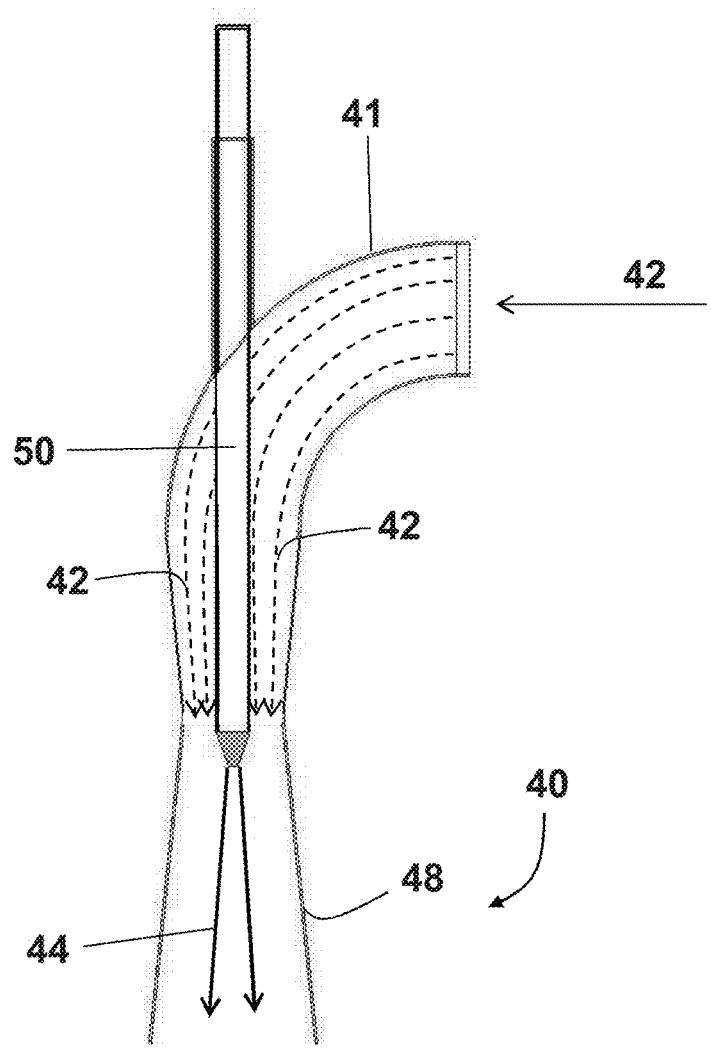
FIG. 5 is an enlarged view of a portion of a drying chamber, shown with a nozzle delivering atomized spray solution into the drying chamber.
Figure 6:
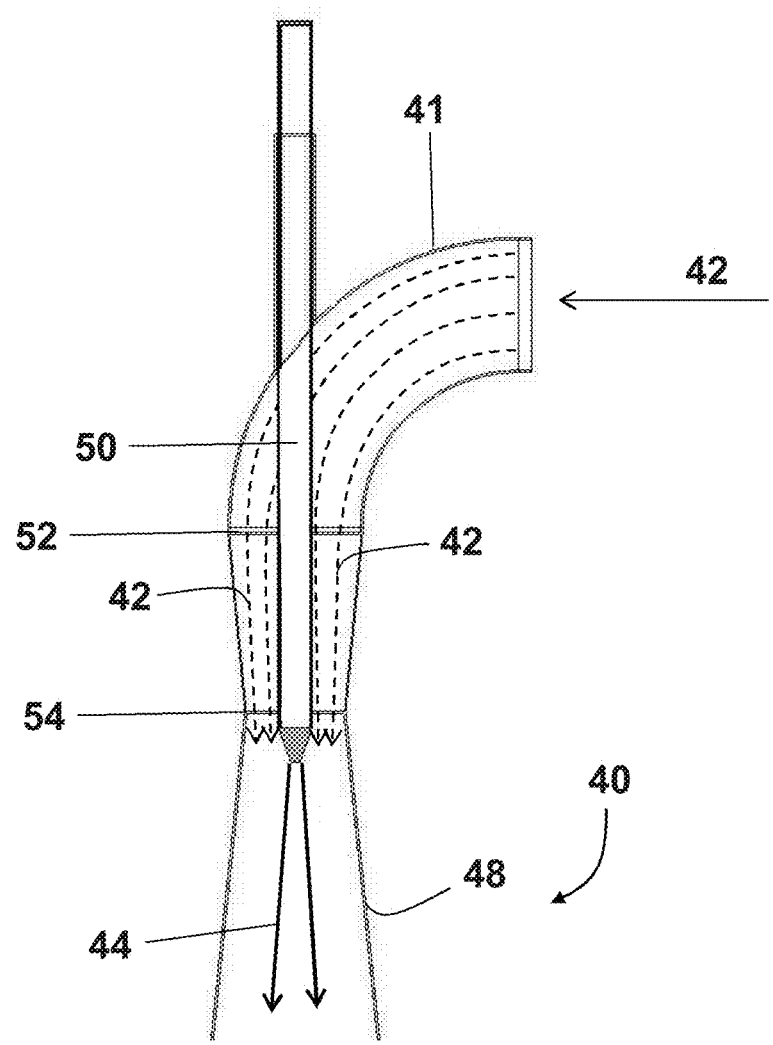
FIG. 6 is an enlarged view of another embodiment of a drying chamber, shown with a nozzle delivering atomized spray solution into the drying chamber.

FIG. 5 illustrates an enlarged view of a nozzle 50 extending into a drying chamber 40. As described above, nozzle 50 can be generally aligned along a center axis of drying chamber 40. Drying gas 42 can be directed into drying chamber 40 and around nozzle 50. In one embodiment, one or more screens can be used to help maintain the central position of nozzle 50 within drying chamber 40. For example, as shown in FIG. 6, first and second mesh screen members 52, 54 can be positioned within the drying gas inlet member to secure nozzle 50 in the desired central position. Mesh screen members 52 and 54 may also be used to help produce substantially parallel flow of the drying gas when it enters the drying chamber 40.

Figure 7:
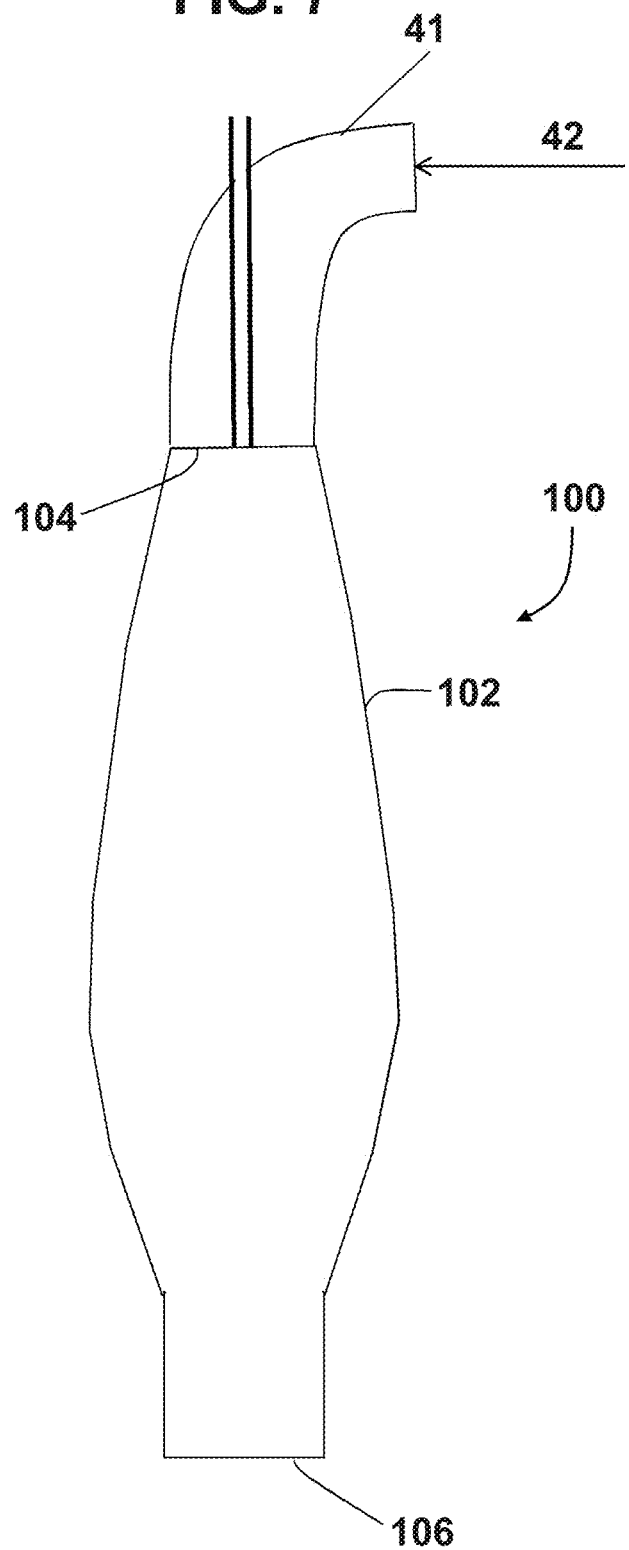
FIG. 7 illustrates another embodiment of a drying chamber.

FIG. 7 illustrates another embodiment of a spray-drying apparatus 100. Spray-drying apparatus 100 is generally similar to spray-drying apparatus 10. Instead of the three distinct regions (A-B, B-C, C-D) shown in FIG. 1, however, spray-drying apparatus 100 has a continuous curvature along the length of the side wall of the drying chamber 102. Like spray-drying apparatus 10, drying chamber 102 can increase in width from a first end 104 towards the center of drying chamber 102 and then decrease in width at a second end 106. Spray-drying apparatus 100, shown in FIG. 7, can have the same general dimensions (e.g., length, maximum and minimum widths, volume) as spray-drying apparatus 10. As described in more detail in the other embodiments, a nozzle can be coupled or secured at first end 104, and a collection member can be coupled or secured to second end 106 to capture at least partially dried particles as they exit the drying chamber 102.

As described above, the spray-drying apparatuses described herein are particularly suitable for producing particles of small average diameters, such as those suitable for inhalation (e.g., less than 10 µm). In other embodiments, however, the particles formed by the spray-drying apparatuses described herein can have an average diameter ranging from 0.5 µm to 500 µm. In another embodiment, the particles have a diameter ranging from 0.5 µm to 100 µm. In another embodiment, the particles have an average diameter of greater than 10 µm. In still another embodiment, the particles have an average diameter of greater than 20 µm. In still another embodiment, the particles have an average diameter of greater than 30 µm.

Spray-Dried Solid Compositions

In one embodiment, the spray-dried product formed by the spray-drying apparatus can comprise an active agent. In another embodiment, the spray-dried product formed by the spray-drying apparatus can comprise an excipient. In another embodiment, the spray-dried product formed by the spray-drying apparatus can comprise an active agent and at least one excipient. The excipient can be used to dilute the active and/or modify the properties of the composition. For instance, for inhalation applications, an excipient may improve or slow the rate of particle dissolution in lung fluid, lung fluid, bronchial mucus, or nasal mucus, reduce particle agglomeration, and/or improve reproducibility of the emitted dose. Examples of excipients include but are not limited to synthetic polymers, polysaccharides, derivatized polysaccharides, sugars, sugar alcohols, organic acids, salts of organic acids, inorganic salts, proteins, amino acids, phospholipids, and pharmaceutically acceptable salt forms, derivatives, and mixtures thereof. In another embodiment, the excipient is selected from polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose (HPMC), hydroxypropyl cellulose (HPC), carboxymethyl ethylcellulose (CMEC), hydroxypropyl methylcellulose acetate succinate (HPMCAS), ethyl cellulose, cellulose acetate, cellulose butyrate, cellulose acetate butyrate, dextran polymer derivatives, trehalose, glucose, sucrose, raffinose, lactose, mannitol, erythritol, xylitol, polydextrose, oleic acid, citric acid, tartaric acid, edetic acid, malic acid, sodium citrate, sodium bicarbonate, albumin, gelatin, acacia, casein, caseinate, glycine, leucine, serine, alanine, isoleucine, tri-leucine, lecithin, phosphatidylcholine, and pharmaceutically acceptable forms, derivatives, and mixtures thereof. In one embodiment, the excipient is selected from lactose, mannitol, trehalose, sucrose, citric acid, leucine, glycine, dextran, oleic acid, and pharmaceutically acceptable salt forms, derivatives, and mixtures thereof. In still another embodiment, the excipient is selected from lactose, mannitol, trehalose, sucrose, citric acid, leucine, glycine, and pharmaceutically acceptable salt forms, derivatives, and mixtures thereof.

The apparatus can be used to form a wide variety of pharmaceutical compositions, including, but not limited to, spray dried amorphous drug, spray dried solid amorphous dispersions, amorphous drug absorbed to a high-surface area substrate, spray dried crystalline drug in a matrix, microparticles, nanoparticles, and spray-dried excipients.

EXAMPLES

Actives Used in Examples

Active Agent 1 was 4-[2-(tert-butylamino)-1-hydroxyethyl]-2-(hydroxymethyl)phenol, also known as salbutamol sulfate, having the structure:

Active Agent 1 is freely soluble in water, and a Log P value of 0.11. The glass-transition temperature ($T_g$) of amorphous Active Agent 1 was determined by DSC to be 125° C.

Active Agent 2 was insulin, a heterotetrameric protein with a pKa of 5.39, Log P 0.22, and melting temperature ($T_m$) of 81° C.

Active Agent 3 was Peptide YY (PYY), a novel 36 amino-acid amidated hormone available from GenScript USA Inc. The peptide is soluble in water.

Example 1

Active Agent 1: Dextran 10

A dry powder consisting of particles of a solid dispersion of Active Agent 1 was prepared by forming a spray solution containing 0.5 wt % Active Agent 1, 1.5 wt % Dextran 10 (Dextran having a molecular weight of 10,000 daltons, available from Amersham Sciences, Piscataway, N.J.), and 98.0 wt % water as follows: the active and solvent were combined in a 500 mL flask and mixed to form a clear solution, then the polymer was added to the solution and mixed for 30 minutes.

The spray solution was pressure fed using 30 psi nitrogen pressure feed from a 1 L pressure vessel to a 2-fluid nozzle (Spray Systems 1650 liquid, 120 air cap). Liquid feed was 25 mL/min, and atomizing nitrogen was 3.0 SCFM at 42 psi into an apparatus substantially similar to that shown in FIG. 1. The inlet nitrogen gas at a flow of 1340 g/min was heated to 155° C. and introduced to the spray dryer. The exit temperature of the drying gas was 55° C. The dried material was pneumatically conveyed through reducing-sized ductwork to a 3-inch outside diameter cyclone. The resulting solid dispersion particles were collected in a 20 mL jar attached to the bottom of the cyclone. The evaporated solvent and drying gas exited the dryer through the top of the cyclone, and were conditioned by a filter and scrubber. The 5.1 g collected of so-formed solid dispersion particles were then dried under vacuum desiccation at room temperature.

Dispersion particles were characterized using a Malvern Particle Size Analyzer, available from Malvern Instruments Ltd. of Framingham, Mass. The data obtained includes Dio, the diameter corresponding to the diameter of particles that make up 10% of the total volume containing particles of equal or smaller diameter, and $D_{90}$, the diameter corresponding to the diameter of particles that make up 90% of the total volume containing particles of equal or smaller diameter. Another parameter is "Span," defined as $$\text{Span} = \frac{D_{90} - D_{10}}{D_{50}},$$

(where $D_{50}$ is the diameter corresponding to the diameter of particles that make up 50% of the total volume containing particles of equal of smaller diameter). Span, sometimes referred to in the art as the Relative Span Factor or RSF, is a dimensionless parameter indicative of the uniformity of the particle size distribution. Generally, the lower the Span, the more narrow the particle size distribution, resulting in improved flow characteristics. The result of the Span determination using Malvern analysis for Example 1 is shown in Table 1.

In Vitro Inhalation Performance

The dry powder was also characterized using the NEXT GENERATION PHARMACEUTICAL IMPACTOR (NGI), Model 170 (available from MSP Corporation, Shoreview, Minn.). The NGI was equipped with a Copley ventilator set at 60 L/min flow for 4 seconds, to draw the spray dried powder into chambers representing the lungs. NGI data include mass median aerodynamic diameter (MMAD) and fine particle fraction (FPF—NGI stages 3 to 8 representing "deep lungs", <4.6 μm)—the fraction of particles that would deposit in the deep lungs, or alveoli. The active dose deposited in the lung can be calculated by multiplying the emitted dose (e.g., the dose delivered by an inhalation device) by the fine particle fraction (deposited dose=emitted dose×FPF).

A 15 mg sample of the solid dispersion particles was evaluated using the NGI. The sample was weighed and loaded into a Quali-V HPMC capsule (size #3). In each chamber of the NGI, 3 drops of silicon oil were added and distributed to all surfaces using a Kimwipe. The HPMC capsule was punctured and attached to the NGI mouth. The chambers were rinsed using 10 mL deionized water, and the samples analyzed using HPLC. The results of the NGI evaluation for Example 1 are shown in Table 1.

Differential Scanning Calorimetry (DSC)

DSC was used to measure the glass transition temperature. The solid dispersion samples were equilibrated for a minimum of 14 hours at ambient temperature and <5% RH, and at ambient temperature and 50% RH. Sample pans were crimped and sealed in an environmental chamber, then loaded into a Thermal Analysis Q1000 Differential Scanning Calorimeter equipped with an autosampler (available from TA Instruments, New Castle, Del.). The samples were heated by modulating the temperature at ±1.5° C./min, and ramping the temperature up to 200° C. at 2.5° C./min. The sample had a single Tg at 125° C. and no other thermal events, suggesting the composition was amorphous.

TABLE 1

| Example | NGI data | | Malvern Dry |
| | FPF* (%) | MMAD** (μm) | Data Span |
| --- | --- | --- | --- |
| 1 | 79 | 2.6 | 1.62 |

*FPF - fine particle fraction
**MMAD - mass median aerodynamic diameter

Example 2

Active Agent 1: Dextran 10

A dry powder consisting of particles of a solid dispersion of Active Agent 1 was prepared by forming a spray solution containing 1.5 wt % Active 1, 0.5 wt % Dextran 10, and 98.0 wt % water as follows: the active and solvent were combined in a 500 mL flask and mixed to form a clear solution, then the polymer was added to the solution and mixed for 30 minutes.

The spray solution was pressure fed using 30 psi nitrogen pressure feed from a 1 L pressure vessel to a 2-fluid nozzle (Spray Systems 1650 liquid, 120 air cap). Liquid feed was 25 mL/min, and atomizing nitrogen was 3.0 SCFM at 42 psi into an apparatus substantially the same as the apparatus shown in FIG. 1. The inlet nitrogen gas at a flow of 1340 g/min was heated to 151° C. and introduced to the spray dryer. The exit temperature of the drying gas was 55° C. The dried material was pneumatically conveyed through reducing-sized ductwork to a 3-inch outside diameter cyclone. The resulting solid dispersion particles were collected in a 20 mL jar attached to the bottom of the cyclone. The evaporated solvent and drying gas exited the dryer through the top of the cyclone, and were conditioned by a filter and scrubber. The 5.4 g of so-formed solid dispersion particles were then dried under vacuum desiccation at room temperature.

Dispersion particles were characterized using the Malvern Particle Size Analyzer, and the results are shown in Table 2.

In Vitro Inhalation Performance

The dry powder was tested using the NEXT GENERATION PHARMACEUTICAL IMPACTOR (NGI), as described above. The results of the NGI evaluation for Example 2 are shown in Table 2.

Differential Scanning Calorimetry (DSC)

DSC was used to measure the glass transition temperature. The solid dispersion samples were equilibrated for a minimum of 14 hours at ambient temperature and <5% RH, and at ambient temperature and 50% RH, and analyzed as described above. The sample had a single Tg at 123° C. and no other thermal events, suggesting the composition was amorphous.

TABLE 2

| | NGI data | | Malvern Dry |
|---|---|---|---|
| Example SDD | FPF* (%) | MMAD** (μm) | Data Span |
| 2 | 74 | 2.6 | 1.50 |

*FPF - fine particle fraction
**MMAD - mass median aerodynamic diameter

Examples 3-5

Active Agent 2: Dextran 10

Examples 3-5 were solid dispersions consisting of 70 wt % Active Agent 2 and 30 wt % Dextran 10. To make Examples 3-5, spray solutions containing 2.1 wt % Active 2, 0.9 wt % Dextran 10, and 97.0 wt % 0.01 N hydrochloric acid were formed by combining the active agent and solvent in a 125 mL flask, mixing to form a clear solution, and adding the polymer with stirring. The pH of the spray solution was adjusted to 7.4 using dilute sodium hydroxide. Prior to spray drying, the solution was diluted with water. For Examples 3 and 4, the final solids concentration in the spray solution was 0.2 wt %. For Example 5, the final solids concentration in the spray solution was 0.8 wt %.

To spray dry the dispersions, the spray solutions were pressure fed using 30 psi nitrogen pressure feed from a 1 L pressure vessel to a 2-fluid nozzle (Spray Systems 1650 liquid, 120 air cap). Liquid feed was 12 mL/min for Example 3, and 25 mL/min for Examples 4 and 5. Atomizing nitrogen was 3.4, 3.5, and 3.6 SCFM (Example 3, 4, and 5) at 52, 56, and 60 psi (Example 3, 4, and 5) into an apparatus substantially the same as that shown in FIG. 1. For Example 3, the inlet nitrogen gas (1320 g/min) was heated to 110° C. and introduced to the spray dryer. For Examples 4 and 5, the inlet nitrogen gas (1350 g/min) was heated to 140° C. and introduced to the spray dryer. The exit temperature of the drying gas for Examples 3, 4, and 5 was 55° C. The dried material was pneumatically conveyed through reducing-sized ductwork to a 3-inch OD cyclone. The resulting solid dispersion particles were collected in a 20 mL jar attached to the bottom of the cyclone. The evaporated solvent and drying gas exited the dryer through the top of the cyclone, and were conditioned by a filter and scrubber. The solid dispersion particles were then dried under vacuum desiccation at room temperature.

Dispersion particles were characterized using the Malvern Particle Size Analyzer, and the results are shown in Table 3.

In Vitro Inhalation Performance

The dry powders were tested using the NGI as described above. The results of the NGI evaluation for Examples 3, 4, and 5 are shown in Table 3.

Controls 1 and 2

Active Agent 2: Dextran 10

Controls 1 and 2 were solid dispersions consisting of 70 wt % Active Agent 2 and 30 wt % Dextran 10, spray-dried as described above, except that a conventional spray dryer was used. To make Controls 1 and 2, spray solutions containing 2.1 wt % Active 2, 0.9 wt % Dextran 10, and 97.0 wt % 0.01 N hydrochloric acid were formed as described above for Examples 3-5. The dispersion of Control 1 was spray-dried without dilution (3.0 wt % solids), and the dispersion of Control 2 was spray-dried following dilution of the spray solution by addition of water, for a final solids concentration of 0.8 wt %. The solutions were spray-dried by directing an atomizing spray using a two-fluid external-mix spray nozzle (Spray Systems 1650 liquid, 120 air cap) at a feed rate of 12.5 g/min into the stainless-steel chamber of a spray dryer (a Niro type XP Portable Spray-Drier with a Liquid-Feed Process Vessel ("PSD-1")), maintained at a temperature of 130° C. at the inlet. The resulting solid dispersions were collected in a cyclone. The dispersions formed using the above procedure were post-dried before further use.

Dispersion particles were characterized using the Malvern Particle Size Analyzer and the NGI, and the results are shown in Table 3. The results in Table 3 show that dispersion particles obtained using the PSD-1 are larger, with a larger span (broader particle size distribution) than dispersion particles obtained using the spray-drying apparatuses disclosed herein. Example 5 and Control 2 provide the closest comparisons, since these dispersions were spray-dried from spray solutions both containing 0.8 wt % solids.

TABLE 3

| Example SDD | NGI data | | Malvern Dry |
| | FPF* (%) | MMAD** (μm) | Data Span |
|---|---|---|---|
| 3 | 90 | ND | 1.32 |
| 4 | 97 | ND | 1.11 |
| 5 | 88 | 1.6 | 1.28 |
| Control 1 | 82 | 2.1 | 1.51 |
| Control 2 | 62 | 2.6 | 1.61 |

*FPF - fine particle fraction
**MMAD - mass median aerodynamic diameter
ND - no data Examples 6 and 7

Active Agent 1: Dextran 10

Examples 6 and 7 were solid dispersions consisting of Active Agent 1 and Dextran 10. To make Example 6, a spray solution was formed containing 0.1 wt % Active 1, 1.9 wt % Dextran 10, and 98.0 wt % water, giving a solid dispersion consisting of 5 wt % Active Agent 1 and 95 wt % Dextran 10. To make Example 7, a spray solution was formed containing 0.2 wt % Active 1, 1.8 wt % Dextran 10, and 98.0 wt % water, giving a solid dispersion consisting of 10 wt % Active Agent 1 and 90 wt % Dextran 10. To spray dry the dispersions, the spray solutions were pressure fed using 30 psi nitrogen pressure feed from a 1 L pressure vessel to a 2-fluid nozzle (Spray Systems 1650 liquid, 120 air cap). Liquid feed was 25 mL/min, and atomizing nitrogen was 3.0 SCFM at 42 psi into an apparatus substantially the same as that shown in FIG. 1. The inlet nitrogen gas (1350 g/min) was heated to 130° C. for Example 6, and 150° C. for Example 7, and introduced to the spray dryer. The exit temperature of the drying gas was 55° C. The dried material was pneumatically conveyed through reducing-sized ductwork to a 3-inch outside diameter cyclone. The resulting solid dispersion particles were collected in a 20 mL jar attached to the bottom of the cyclone. The evaporated solvent and drying gas exited the drier through the top of the cyclone, and were conditioned by a filter and scrubber. The solid dispersion particles were then dried under vacuum desiccation at room temperature.

Dispersion particles were characterized using the Malvern Particle Size Analyzer and the NGI, and the results are shown in Table 4.

TABLE 4

| Example SDD | NGI data | | Malvern Dry |
| | FPF* (%) | MMAD** (μm) | Data Span |
|---|---|---|---|
| 6 | 65 | 2.8 | ND |
| 7 | 69 | 2.6 | 2.8 |

*FPF - fine particle fraction
**MMAD - mass median aerodynamic diameter
ND - no data Examples 8 and 9

Active Agent 3: Dextran 10

Examples 8 and 9 were solid dispersions consisting of 70 wt % Active Agent 3 and 30 wt % Dextran 10. To make Example 8, a spray solution containing 2.0 wt % Active 3, 0.9 wt % Dextran 10, and 97.1 wt % water was formed by combining the active and solvent in a 125 mL flask, mixing to form a clear solution, and adding the polymer with stirring. The pH of the spray solution was adjusted to 6.4 using dilute sodium hydroxide. Prior to spray drying, the solution was diluted to 1.5 wt % solids with water. To make Example 9, a spray solution containing 1.0 wt % Active 3, 0.4 wt % Dextran 10, and 98.6 wt % water was formed by combining the active and solvent in a 125 mL flask, mixing to form a clear solution, and adding the polymer with stirring. The pH of the spray solution was adjusted to 6.6 using dilute sodium hydroxide. There was no dilution of the spray solution prior to spray drying. To spray dry the dispersions, the spray solutions were pressure fed using 30 psi nitrogen pressure feed from a 1 L pressure vessel to a 2-fluid nozzle (Spray Systems 1650 liquid, 120 air cap). Liquid feed was 25 mL/min, and atomizing nitrogen was 3.3 SCFM at 45 psi into an apparatus substantially the same as that shown in FIG. 1. The inlet nitrogen gas (1350 g/min) was heated to 143° C. for Example 8, and 118° C. for Example 9, and introduced to the spray dryer. The exit temperature of the drying gas was 55° C. The dried material was pneumatically conveyed through reducing-sized ductwork to a 3-inch outside diameter cyclone. The resulting solid dispersion particles were collected in a 20 mL jar attached to the bottom of the cyclone. The evaporated solvent and drying gas exited the drier through the top of the cyclone, and were conditioned by a filter and scrubber. The solid dispersion particles were then dried under vacuum desiccation at room temperature.

Dispersion particles were characterized using the NGI, and the results are shown in Table 5.

TABLE 5

| Example SDD | NGI data | |
| | FPF* (%) | MMAD** (μm) |
|---|---|---|
| 8 | 80 | 2.06 |
| 9 | 80 | 1.84 |

*FPF - fine particle fraction
**MMAD - mass median aerodynamic diameter

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of spray drying, comprising:

forming a plurality of droplets by atomizing a spray solution using a nozzle positioned at the first end of the drying chamber, the drying chamber further comprising a second end and at least one side wall extending between the first and second ends to define an interior of the drying chamber and having a center axis, wherein at least a portion of the at least one side wall that surrounds the nozzle at the first end of the drying chamber extends away from the center axis at a first angle relative to the center axis, the first angle being at least 5° but less than 45°, and wherein a ratio of the length between the first and second ends to a maximum width between opposing internal surfaces of the interior of the drying chamber is at least 5 to 1;

delivering the plurality of droplets into the drying chamber;

delivering drying gas into the drying chamber to at least partially dry the plurality of droplets to form a plurality of particles; and directing the plurality of particles out of the drying chamber, wherein said spray solution comprises at least one active agent, at least one excipient, and at least one solvent.

2. The method of claim 1, wherein the droplets are delivered into the drying chamber at a maximum spray pattern angle relative to the center axis of less than 45°.

3. The method of claim 1, wherein the first angle is at least 5° but less than 30° relative to the center axis.

4. The method of claim 1, wherein the nozzle is configured to atomize a liquid into the drying chamber at a maximum spray pattern angle relative to the center axis of less than 30°.

5. The method of claim 1, wherein the first angle is at least 5° but less than 20° relative to the center axis.

6. The method of claim 1, wherein the droplets are delivered into the drying chamber at a maximum spray pattern angle relative to the center axis of less than 20°.

7. The method of claim 1, wherein the particles formed by the nozzle have a mass median aerodynamic diameter of less than 10 microns.

8. The product of the method of claim 1, wherein the particles are inhalable particles.

9. A method of spray drying, comprising:

forming a plurality of droplets by atomizing a spray solution using a nozzle positioned at the first end of the drying chamber, the drying chamber further comprising a second end and at least one side wall extending between the first and second ends to define an interior of the drying chamber and having a center axis, wherein at least a portion of the at least one side wall that surrounds the nozzle at the first end of the drying chamber extends away from the center axis at a first angle relative to the center axis, the first angle being at least 5° but less than 45°, and wherein a ratio of the length between the first and second ends to a maximum width between opposing internal surfaces of the interior of the drying chamber is at least 5 to 1;

delivering the plurality of droplets into the drying chamber;

delivering drying gas into the drying chamber in substantially parallel flow to at least partially dry the plurality of droplets to form a plurality of particles; and directing the plurality of particles out of the drying chamber, wherein, said spray solution comprises at least one active agent, at least one excipient, and at least one solvent.

10. The method of claim 9, wherein the droplets are delivered into the drying chamber at a maximum spray pattern angle relative to the center axis of less than 45°.

11. The method of claim 9, wherein the first angle is at least 5° but less than 30° relative to the center axis.

12. The method of claim 1, wherein the particles have an average diameter ranging from 0.5 μm to 500 μm.

13. The method of claim 1, wherein the excipient is selected from synthetic polymers, polysaccharides, derivatized polysaccharides, sugars, sugar alcohols, organic acids, salts of organic acids, inorganic salts, proteins, amino acids, phospholipids, and pharmaceutically acceptable salt forms, derivatives, and mixtures thereof.

14. The method of claim 1, wherein the excipient is selected from polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose (HPMC), hydroxypropyl cellulose (HPC), carboxymethyl ethylcellulose (CMEC), hydroxypropyl methylcellulose acetate succinate (HPMCAS), ethyl cellulose, cellulose acetate, cellulose butyrate, cellulose acetate butyrate, dextran polymer derivatives, trehalose, glucose, sucrose, raffinose, lactose, mannitol, erythritol, xylitol, polydextrose, oleic acid, citric acid, tartaric acid, edetic acid, malic acid, sodium citrate, sodium bicarbonate, albumin, gelatin, acacia, casein, caseinate, glycine, leucine, serine, alanine, isoleucine, trileucine, lecithin, phosphatidylcholine, and pharmaceutically acceptable forms, derivatives, and mixtures thereof.

15. The method of claim 1, wherein said solvent is selected from water, methanol, ethanol, n-propanol, isopropanol, butanol, acetone, methyl ethyl ketone, methyl isobutyl ketone, ethyl acetate, propyl acetate, tetrahydrofuran, acetonitrile, methylene chloride, toluene, 1,1,1-trichloroethane, dimethyl acetamide, dimethylsulfoxide, or mixtures and combinations thereof.

16. The method of claim 1, wherein said active agent is selected from a small molecule, having a molecular weight of 2000 Daltons or less.

17. The method of claim 1, wherein said active agent is selected from proteins, antibodies, antibody fragments, peptides, oligonucleotides, vaccines, and various derivatives of such materials.

18. The method of claim 1, wherein said active agent comprises two or more active agents.

19. The method of claim 1, wherein said solvent is selected from water, methanol, ethanol, n-propanol, isopropanol, butanol, acetone, methyl ethyl ketone, methyl isobutyl ketone, ethyl acetate, propyl acetate, tetrahydrofuran, acetonitrile, methylene chloride, toluene, 1,1,1-trichloroethane, dimethyl acetamide, dimethylsulfoxide, or mixtures and combinations thereof.

20. The method of claim 1, wherein said particles have an average diameter ranging from 0.5 μm to 100 μm.

* * * * *